United States Patent [19]
Caldarise

[11] Patent Number: 5,716,414
[45] Date of Patent: Feb. 10, 1998

[54] CERAMIC/METALLIC ARTICULATION COMPONENT AND PROTHESIS

[75] Inventor: Salvatore Caldarise, Hanson, Mass.

[73] Assignee: Johnson & Johnson Professional, Inc., Raynham, Mass.

[21] Appl. No.: 798,492

[22] Filed: Feb. 10, 1997

Related U.S. Application Data

[63] Continuation of Ser. No. 469,800, Jun. 6, 1995, abandoned, which is a continuation of Ser. No. 234,267, Apr. 28, 1994, abandoned.

[51] Int. Cl.$^6$ .................................................. A61F 2/28
[52] U.S. Cl. .................................... 623/16; 623/18
[58] Field of Search .................... 623/16, 18, 66; 164/98, 103; 428/621

[56] References Cited

U.S. PATENT DOCUMENTS

| | | | |
|---|---|---|---|
| 3,605,123 | 9/1971 | Hahn | 3/1 |
| 4,033,400 | 7/1977 | Gurwell et al. | 164/98 |
| 4,146,936 | 4/1979 | Aoyagi et al. | 623/23 |
| 4,281,420 | 8/1981 | Raab | 3/1.912 |
| 4,314,381 | 2/1982 | Koeneman | 3/1.912 |
| 4,365,359 | 12/1982 | Raab | 3/1.912 |
| 4,722,870 | 2/1988 | White | 428/621 |
| 4,794,046 | 12/1988 | Nagai | 428/312.2 |
| 4,846,837 | 7/1989 | Kurze et al. | 623/16 |
| 4,969,913 | 11/1990 | Ojima | 623/66 |
| 4,976,736 | 12/1990 | White et al. | 623/16 |
| 5,002,579 | 3/1991 | Copf et al. | 623/23 |
| 5,059,209 | 10/1991 | Jones | 623/23 |
| 5,108,435 | 4/1992 | Gustavson et al. | 623/16 |
| 5,167,271 | 12/1992 | Lange et al. | 164/103 |
| 5,204,055 | 4/1993 | Sachs et al. | 419/2 |
| 5,211,664 | 5/1993 | Tepic et al. | 623/16 |
| 5,219,363 | 6/1993 | Crowninshield | 623/23 |
| 5,236,457 | 8/1993 | Devanathan | 623/16 |
| 5,308,412 | 5/1994 | Shetty et al. | 148/238 |
| 5,330,826 | 7/1994 | Taylor et al. | 428/216 |

*Primary Examiner*—Michael J. Milano
*Attorney, Agent, or Firm*—Nutter, McClennen & Fish, LLP

[57] ABSTRACT

An implantable bone prosthesis includes portions of two different materials which interfit with each other to form a unitary article having hard wear surface portions and strong, stiff portions for structural support. These portions are preferably formed of ceramic and of metal, respectively. The prosthesis is formed by making a multiply connected ceramic wear surface element having openings or passages therethrough, and casting the remainder of the prosthesis extending in the openings to form a mating or dendritic support or a frame interdigitated and interlocked with the ceramic wear surface. The frame may be shaped so that it contracts along a direction of shrinkage, as the casting cools, without binding against the ceramic body. In a spherical shell, such as used for the weight-bearing acetabular shell or ball joint of a hip, this is achieved with short, radially-directed interlock elements. Other connections of the two materials may include tapered bores, dovetail channels, fern-like dendritic structures, or the like. Ball and socket, trunion and other articulations are fabricated with high strength and durable wear properties.

13 Claims, 5 Drawing Sheets

CERAMIC/METALLIC ARTICULATION COMPONENT AND PROTHESIS

This application is a continuation of application Ser. No. 08/469,800 filed Jun. 6, 1995, abandoned, which is a continuation of application Ser. No. 08/234,267, filed Apr. 28, 1994, abandoned.

BACKGROUND OF THE INVENTION

This invention relates to implantable articles and methods for manufacturing such articles. More particularly, the invention relates to bone prostheses and processes for their manufacture.

There are known to exist many designs for and methods of manufacturing implantable bone prostheses. Bone prostheses include components of artificial joints, such as elbows, hips, knees, and shoulders. An important consideration in the design and manufacture of implantable prostheses of this type is that the prosthesis have adequate fixation when implanted within the body, be structurally strong, and in articulation areas, have hard, long lasting wear surfaces.

Early designs of implantable articles relied upon the use of cements, such as polymethylmethacrylate to anchor the implant to surrounding bone, or to anchor pieces of the implant to each other. The use of such cements can have some advantages, such as enhancing the range of fit while providing an immediate and secure fixation that does not develop free play, or lead to erosion of the joining bone faces post operatively. However, the current trend is to use these cements to a lesser extent because of their tendency to lose adhesive properties over time and the possibility that the cements contribute to wear debris within a joint. Recently, implantable bone prostheses have been designed such that they encourage the growth of trabecular bone tissue around the implant, principally by arranging that the surface of the implantable bone prosthesis is irregular or textured in a defined way. The promotion of newly-formed hard tissue in and around the textured surface of the prosthesis has been found to provide good fixation of the prosthesis within the body. A greater degree of bone fixation can usually be achieved where bone contacting surfaces of an implantable prosthesis are more porous or irregular.

Such porous or irregular surfaces can be provided in implantable articles by a variety of techniques. In some instances, an irregular surface pattern or surface porosity is formed by embossing, chemical etching, milling or other machining operations, or plasma spray metallization. Textured surfaces are also applied by joining one or more separate surface plate inserts to an exterior surface of the prosthesis to provide separate porous or pore-forming surfaces. Separate pore-forming surfaces can be joined to or formed on an implantable bone prosthesis by sintering metal particles or powder to a surface of the prosthesis, or textured surfaces may be formed by soldering wire-based pads or grids to provide the desired relief surface features.

Similarly, wear surfaces of an articulation component are required to be smooth and hard, and a number of techniques have been developed to arrange that those regions of a bone prosthesis have appropriate surface properties. Ceramic material has many desirable properties for this application, since it is extremely hard, may be highly polished and is biologically inert. Unfortunately, a bone prosthesis made entirely of ceramic is subject to breakage, while ceramic coatings selectively placed on a metal prosthesis may be subject to cracking, chipping or spalling. If one attempts to overcome these problems by forming a set of ceramic portions of a prosthesis as blocks that are fitted into machined bores or dovetails of the metal prosthesis, one is limited to rather simple constructions, dictated by the available machine shapes.

As an intermediate approach, various surface hardening techniques have been proposed for metal prostheses, such as carbide or nitride surface treatments of the metal. Ion beam bombardment has also been proposed to enhance the depth of such surface transformation. These approaches, however, while providing greater toughness and fracture resistance than fired-on or cemented ceramic surface elements, affect only a very thin surface layer, typically under several micrometers deep. They also involve relatively costly and complex equipment and fabrication processes.

For production runs, implantable articles such as bone prostheses are preferably made by an investment casting process. In general, investment casting first requires the making of a solid model of the article to be cast, the model being made from a meltable casting wax through a molding operation such as injection molding. Once the solid model is made, one or more of the solid models are fixed to a wax tree, which is then encased, along with the attached models, in a refractory binder material to form runners interconnecting mold cavities filled with wax. After repeatedly dipping the assembly in a ceramic slurry coating and drying the coating between dips to form a wax-filled green shell, which is dried, the shell is heated to a temperature sufficient to melt and extract the casting wax from within. Thereafter, the shell may be sintered or fired at an even higher temperature, to form a refractory ceramic mold. High temperature heating also burns off any residues. Molten metal is then poured into the investment assembly to entirely fill the cavities once occupied by the wax and to form cast articles having the shape of the hollows left by the wax models. This process may be used to make strong metal bone prostheses, which may subsequently have their bearing surfaces treated or covered to form hardened regions, in the manner discussed above.

As is apparent from the foregoing discussion, the processes for making an implantable prosthesis currently involve many distinct steps in which, for example, different operations of casting, machining, heating and surface treatment or coating may be required in order for a single component to possess a body with acceptable strength and a surface with acceptable wear characteristics. Accordingly, there is a need for bone prostheses having improved load bearing and surface wear characteristics. There is also a need for improved methods of manufacturing prostheses having such characteristics.

It is thus an object of the invention to provide an implantable article, such as an implantable bone prosthesis having a strong body and long-wearing surface characteristics.

It is also an object of the invention to provide an implantable bone prosthesis that integrally combines hard exterior surfaces with structural strength and rigidity.

Another object of the invention is to provide casting techniques that enable the manufacture of implantable bone prostheses of hybrid structure having two or more materials of dissimilar properties.

Another object of the invention is to manufacture bone prostheses having two or more dissimilar materials which are interconnected in a high temperature process into a unitary body having reduced internal strain yet great structural strength and surface hardness.

The manner in which the invention attains these and other objects will be understood from the description that follows.

SUMMARY OF THE INVENTION

The foregoing objects are achieved in a bone prosthesis and a method of making the prosthesis wherein at least a portion of the prosthesis has an as-cast structure of mutually interfitted ceramic and metal portions. Preferably, the ceramic portions include at least a bearing surface, while the metal portions extend at least in part through the ceramic portion, or vice-versa. The process of manufacture includes the steps of making a mold surface element, which may be a multi-tunnel block having a desired surface shape and/or finish, or may be a small plate or shell, by a three-dimensional printing process of building up the surface element in layers. A powder material of suitable composition is laid down layer by layer and a portion of each layer is solidified by applying a binder material in selected regions thereof. Collectively, the solidified layers form a multiply-connected object, that is, one having one or more holes or openings in it, and have at least one exterior bearing surface. The "green" object formed in this manner is then dried and fired to form a ceramic body with a hard exterior wear surface. A hybrid prosthesis is then formed by filling the ceramic body with a casting metal so that the completed prosthesis retains at least the wear surface portion of the ceramic body as its exterior wear surface, and has an interfitted cast metal portion constituting a structural frame or support among non-wearing portions of the prosthesis.

Preferably, open and closed mold surfaces or bodies of this type are printed by an imagewise deposition of binder material in consecutive layers of powder, wherein a computer-controlled scanner and feed mechanism define the shape of the ceramic body and wear surface, having extensions or passages configured to interlock with the metal passed therein and forming part of the finished prosthesis. Different ceramic-forming powder materials as well as binders may be used to build ceramic bodies in which high temperature alloys are cast. Modified lost wax processes allow the use of connected arrays of printed wear surface elements and molds to efficiently cast many prostheses at once. The metal and ceramic portions have different thermal characteristics, and they are configured in specific interfitting shapes that minimize stress defects in each mass of material when the casting cools. In a spherical article, concentric metal portions and ceramic portions form a unitized body anchored by radially disposed protrusions, that shrink without binding as they cool to create a firm interlock free of tensile and bending stresses. Linearly-extending tapered or tree-like metal skeletons may provide structural support without introducing casting stresses.

BRIEF DESCRIPTION OF THE DRAWINGS

The foregoing and other objects of this invention, the various features thereof, as well as the invention itself, may be more fully understood from the following description, when read together with the accompanying drawings, in which.

DETAILED DESCRIPTION OF THE INVENTION

The invention will be described with specific reference to a femoral stem and ball joint, with the acetabular shell component as an example of the wear surface in an implantable bone prosthesis.

Figure 1:
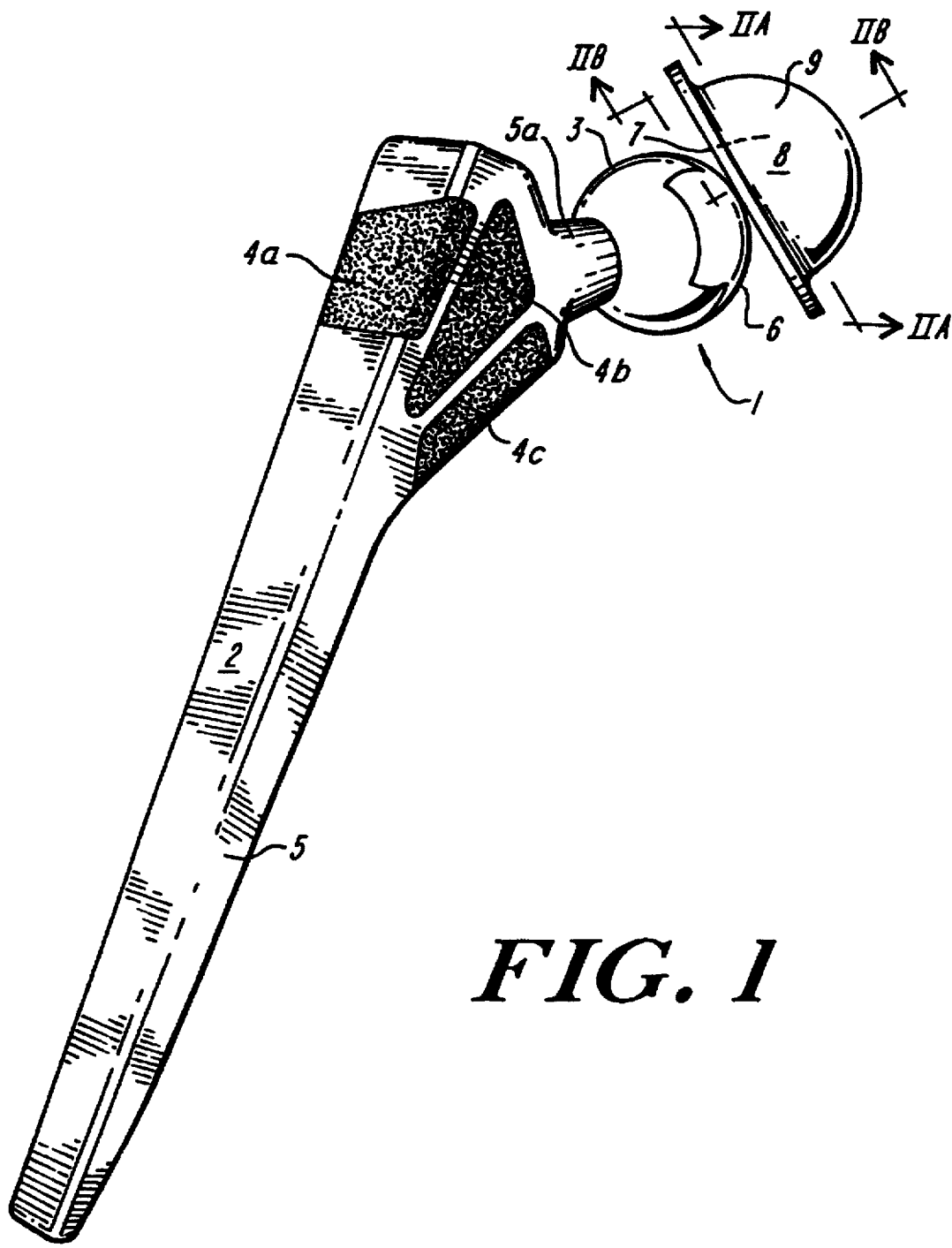
FIG. 1 is a side perspective view of a femoral stem and acetabular shell for human hip prosthesis.

As illustrated in FIG. 1, the prosthesis 1 includes a stem 2 having an articulation in the form of a ball 3 at one end, and a shell 8 which receives the ball and provides the upper component of a bearing surface. As will be appreciated, a patient may receive one or more components in a given operation. Stem 2 comprises a shank portion 5 which is inserted into a prepared opening at the end of the femur, the stem having textured body surface regions 4a, 4b, 4c adapted to promote trabecular bone growth and a neck 5a to which the ball 3 attaches. Ball 3 has a convex wear surface 6 which as illustrated is generally spherical in shape. In one form of such prosthesis currently on the market, the ball is mounted to the neck of the stem via a Morse-tapered coupling, which allows the ball and stem portions 3, 2 to be separately fabricated and finished, and to be assembled together during surgical installation. Shell 8 is a generally hemispherical shell with an internal concave surface having a radius of curvature matching that of ball 3, so that when assembled together, the ball rides within the shell without contact on a lubricating layer of fluid which is quite thin. Shell 8 comprises an inner wear surface 7 which, as described more fully below, is preferably formed of ceramic material, and an outer structural body 9 which gives the unit toughness, rigidity and structural strength. Body 9 may, for example, be made of a cobalt chromium alloy or other strong biocompatible metal suitable for this purpose.

In accordance with the principal aspect of the present invention, wear surfaces of the prosthesis, namely the outer surface of ball 3 and the inner surface of shell 8, are formed of one or more materials having high wear characteristics, while the supporting or structural strengthening portions of the device are formed of a second material having what may be described as "structural" characteristics. The "structural" characteristics generally include stiffness, toughness and high strength, but may also include properties such as ductility, resilience or the like. Furthermore, the two different materials are combined and unified in a single structure by being interfitted together with at least one region of the material having openings or holes in it to receive the other, thus being multiply connected in the topological sense and interfitting to form a single body. Thus, for example, rather than simply having a plate of one material dovetailed into a groove or dropped into a counterbore in a body formed of another material, the present invention envisages one or more tunnels, channels or bores extending into a body, possibly along a curved or knotted contour which either could not be cut by machine techniques, or could not be filled with a solid counterpart, and a second material filling these openings and interfitted with the body into a unitized article.

This construction is achieved in accordance with one aspect of the present invention by novel processes for manufacturing a prosthetic article having the interconnected fillable regions described herein. In particular, a novel method for making an implantable bone prosthesis having an integral, as-cast hybrid or two-material construction, employs a computer-controlled three-dimensional printing technique to build a ceramic casting wear body and then directly casting metal into at least a portion of the body to form the desired prosthesis. The casting body is built up of loose powder applied in successive layers, with a binder applied at one or more points, contours, or regions of each layer, using a computer-controlled scanning nozzle similar to an ink jet, to selectively solidify the powder in each layer in a region or profile corresponding to the section through the intended three-dimensional article at that layer. Once the wear body is made, a metal portion is cast into and securely interfitted with it to form a hybrid metal-ceramic prosthesis.

General three-dimensional printing techniques which are suitable for the practice of the invention are disclosed in U.S. Pat. No. 5,204,055 to Sachs et al., which patent is hereby expressly incorporated herein by reference. In accordance with the present invention, investment casting molds, bodies or lining plates are manufactured using such powder printing in specialized three-dimensional patterns, so that metal cast into and against the body or lining plate interfits with a ceramic part which is to be a wear surface of the finished article.

The "printing" process involves the deposition of a layer of a powder material in a confined area and the application of a binding material to selected regions of the powder layer to solidify it in those regions. A next layer of powder is then deposited over the first layer, and binding material is again applied to selected, generally partially overlapping, regions of the second layer of powder to solidify it in those new regions and to bind the solidified sections to the previously solidified sections of the layer below. These steps are repeated under computer control of the scanning and binder devices according to a predetermined pattern to form a solid object formed of many successive laminations of powder and binding material. The regions in which binder material is deposited in each scan layer correspond to the sections, at the current scan height, of the three-dimensional object being formed. As described further below, this object comprises a body portion, which is to become the ceramic wear surface portion of a prosthesis, and may also include all or part of a surrounding mold surface, which may, for example, constitute a cup-shaped cavity, into which the complementary-shaped metal article, such as the stem of a femoral prosthesis, or the structural body of an acetabular shell, is cast.

A broad range of contour, shape or surface texture may thus be imparted to the cast article. In practice, the extent of detail and complexity which can be attained in objects manufactured using three-dimensional printing processes is limited by the resolution of the binder application mechanism that applies the binding material to the powder layer to form detailed or complex patterns. Using computer control, virtually any three-dimensional design which can be scanned or interpreted by a computer may be reproduced, regardless of its complexity, subject to the resolution limit. Resolution for the powder consolidation three-dimensional printing can be achieved by modifying the techniques and materials of the aforesaid Sachs '055 patent, with a feature size below 0.2 millimeters, and this limit is subject to improvement with adjustment of the layer thickness, scan nozzle geometry, powder size, binder viscosity and powder wetting properties, as will be appreciated by those familiar with the process.

A more detailed description of the fabrication of ceramic molds and multi-mold investment casting techniques appears in the commonly-owned U.S. patent application Ser. No. 08/198,874 and filed in the United States Patent and Trademark Office on Feb. 18, 1994 entitled: Implantable Articles With As-Cast Macrotextured Surface Regions and Method of Manufacturing the Same, of which applicant is a co-inventor, the disclosure of which is hereby incorporated by reference. That application describes suitable materials for forming ceramic bodies, and a method for making these bodies in complex and varied shapes for casting prostheses. The present patent application goes beyond the disclosure of that document in applying such three-dimensional powder printing technology to form such shapes of ceramic-forming materials, which are fired to form ceramic bodies with a wear surface. These are cast together with and penetrated by a metal, and are firmly interlocked so that the ceramic bodies remain part of the finished prosthesis. As described in greater detail below, the shapes of each may be selected to maximize the desirable mechanical properties of each component, may interfit to reduce mechanical stress, or may interconnect to assure integrity of the hybrid prosthesis.

Figure 2B:
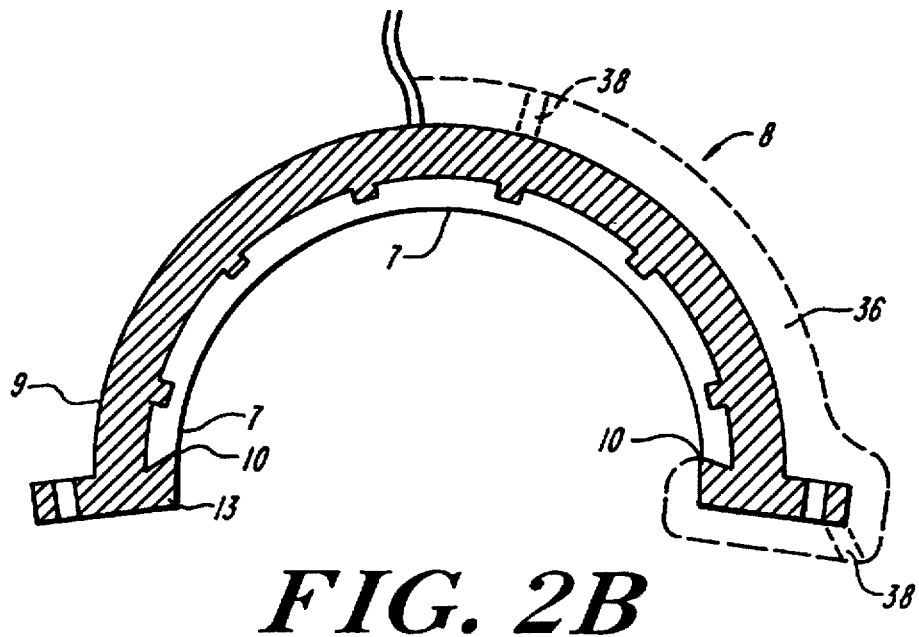
FIGS. 2A, 2B are sections through the shell of FIG. 1.
Figure 2A:
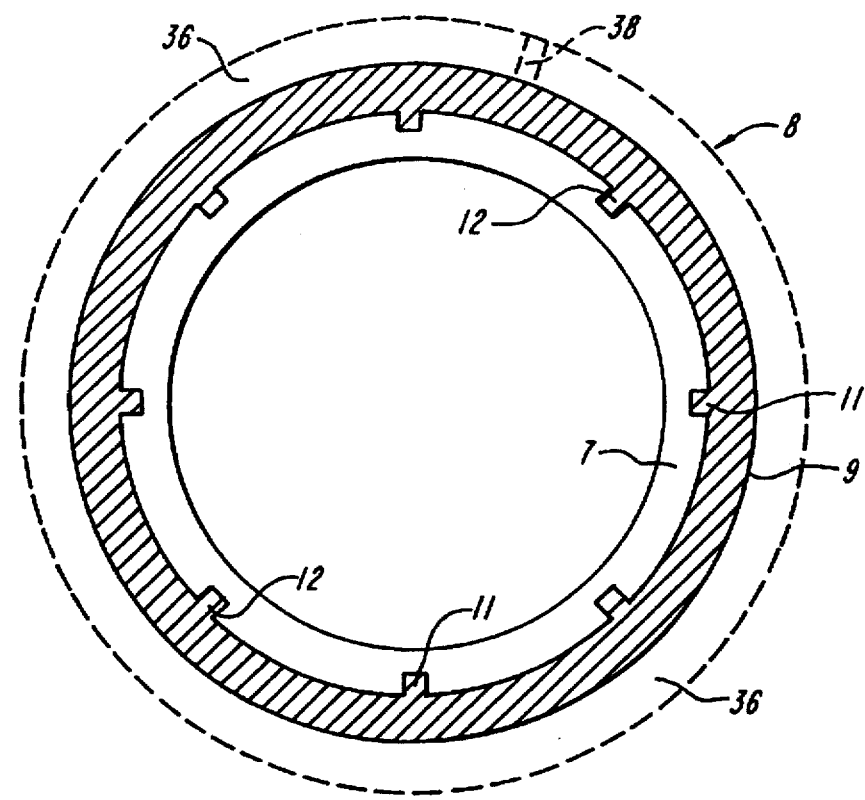

FIGS. 2A and 2B indicate sections in the planes depicted in FIG. 1 through the acetabular shell 8 of that FIGURE. As shown, the inner wear surface 7 and the outer structural body 9 lie in shells parallel to and contiguous to each other over the full extent of their areas along a generally spherical interface. A plurality of nubs 11 extend from one portion into corresponding recesses or openings 12 in the other so that the two shells remain fixedly aligned in registry and attached to each other.

As noted above, portion 7 is preferably a ceramic, whereas portion 8 is cast as molten metal against the outer (non-contact bearing) face of the ceramic. Because both members have a spherical shape, the high temperature processes envisaged with their formation—namely, the casting of molten metal at a temperature of over a thousand degrees followed by its shrinkage down to room temperature in contact with the ceramic wear surface element 7—results in a relative motion between the two components in purely radial direction. Since each nub 11 is oriented along a radial projection, as the casting shrinks upon cooling, relative motion that occurs along the direction of shrinkage is purely radial, and this special shape simply allows the nubs 11 to move along the openings 12 in the mating ceramic member. Thus, rather than causing laterally directed shear forces, or bending or tensile forces which could warp or crack the delicate ceramic, the post-casting thermal cool-down effects, although substantial, produce no shear coupling, bending stress, or tensile stress in the ceramic portions of the article, but rather induce at worst a small compressive force on the inner element. Rather than binding against fixed structures and building up tensile forces, the nub 11 may slide harmlessly back and forth along the radial direction in the channels or indentations 12 in the mating part of the prosthesis, and the alignment and integrity of the article as a whole is preserved without creating stresses in the structure. Also of note in FIG. 2B is the protruding rim 13 of the outside metal body 9 in the region 10 at edges of the ceramic wear surface. This contains and shields the edge of the ceramic wear surface against chipping, and further strengthens the outer shell 9 in the manner of an I-beam against flexing and bending.

In addition to the relatively simple construction of FIGS. 2A and 2B for eliminating tensile and bending stresses in a hybrid two-material two-layer spherical shell, the invention contemplates a variety of different configurations of interlocking ceramic and metal portions in prostheses of larger solids, or less geometric or regular shapes, such as the shapes of the femoral stem and ball, 2, 3 of FIG. 1.

In accordance with a preferred aspect of the present invention, wear surfaces, such as the upper portion of ball 3 are ceramic while all or a major continuous part of long members, such as stem 2, are metal, the two portions, metal and ceramic, being interfitted in such a way that the ceramic does not extend for any considerable length in either an unsupported or unreinforced state, or in a structure so thin that it would be subject to an undesirably large bending motion, or in a structure so rigidly interlocked that it would be subject to large thermal cool-down stresses.

Figure 3:
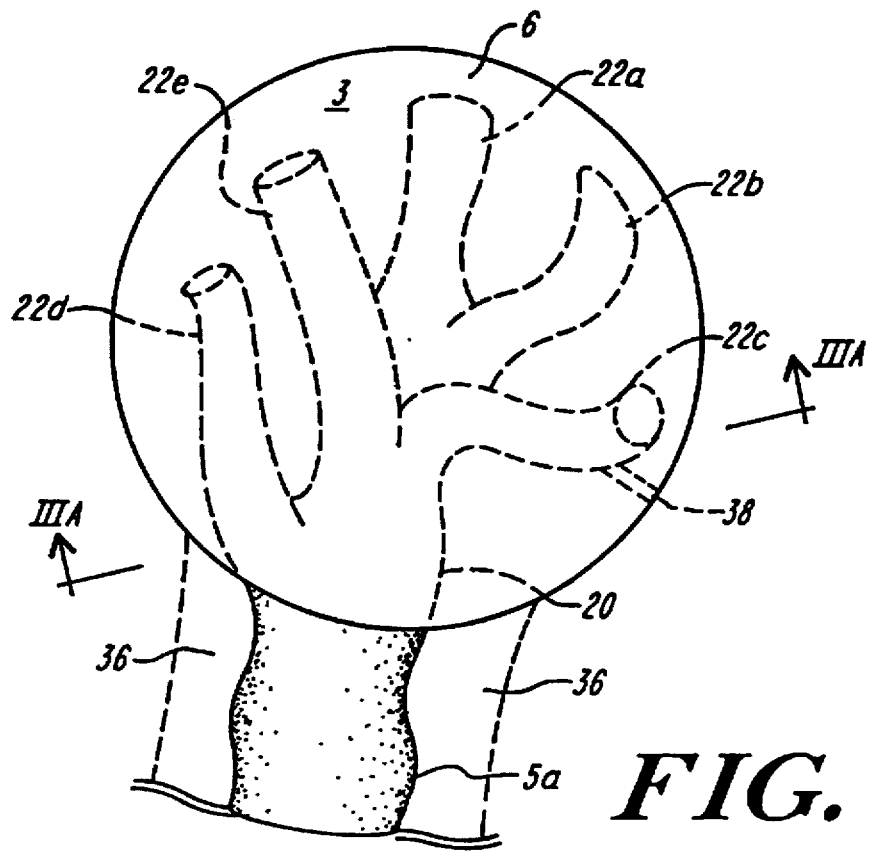
FIGS. 3 and 3A show details of a ball for a femoral stem such as the stem of FIG. 1.

As shown in FIG. 3, these constraints are satisfied in one embodiment of a femoral stem and ball construction, wherein the ball 3 is formed as a ceramic body having multiple internal apertures in the form of meandering tunnels into which the metal is cast, to form a rigid skeleton in the form of a series of small branch-like fingers, shells, or dendrites 22a, 22b . . . etc. connected to a common large branch or trunk 20. The fingers 22a, 22b . . . provide support along a broad interior area of the ball without separating the ceramic portion into parts so isolated or thin that they might develop large cracks under the stresses they encounter in use.

Figure 3A:
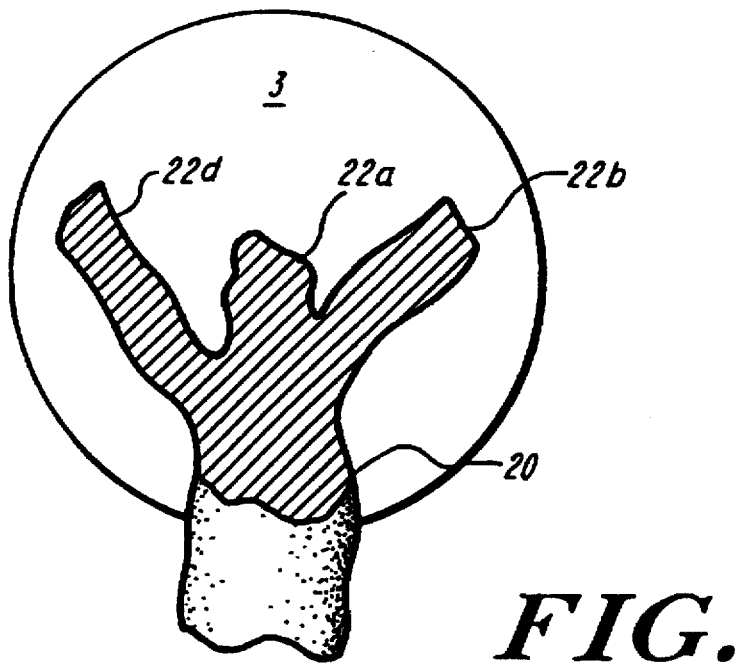
Figure 3B:
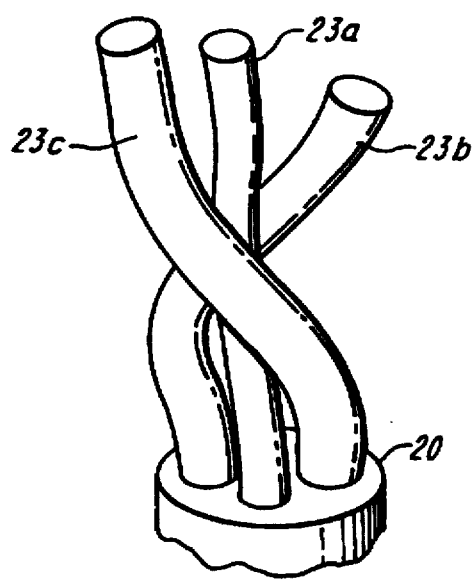
FIGS. 3B and 3C illustrate other embodiments of such a ball.

The fingers fan outwardly within the ball, so that once cast in place, the inner metal is securely affixed to the ball. Moreover, since each finger 22i is cantilevered out from a main branch or trunk 20, the stresses of contraction as the casting cools are directed axially along the finger do not transmit shear forces to or result in destructive fracture of the surrounding ceramic. As shown in FIG. 3A, a given planar section through the completed article may cut across the full width of one or more small branches 22b, 22d, may partially intercept a branch 22a curving outside the plane of the section, and may entirely miss some branches 22c, 22e directed outwardly from branch 20 in other directions. Thus, the branching finger structure is a space-filling skeleton which distributes load and prevents fracture of the excessively stiff and brittle ceramic. Other simple forms of metal framework or skeleton may be devised that also avoid introducing shear or tensile forces in the structure, such as slightly-divergent helically-intertwined branches 23a, 23b, 23c as shown in FIG. 3B. At their other end, rather than emanating from a solid trunk, the branches may, for example, collectively converge to a narrow rigidly intertwined bundle to form the stem of the prosthesis.

Figure 3C:
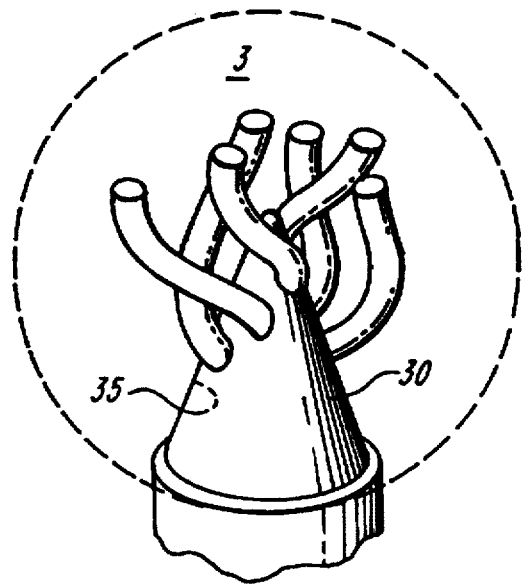

As shown in FIG. 3C, the cast support or structured center of ball 3 may include a thimble shaped metal shell 30 which has a standard size Morse tapered interior surface 35 for attaching to a conventional femoral stem, the shell 30 having a plurality of arms or protrusions that radiate through the ceramic ball 3 to fixedly interconnect the tapered socket casting to the surrounding ceramic material.

As discussed above, the formation of a metal skeleton or framework within a ceramic member, or supporting or underlying ceramic portions of a cast member, is preferably accomplished by casting the metal into openings in the ceramic. It thus involves a stable shell or mold during the casting steps positioned around the ceramic block, sphere or other surface wear elements, so that the shell or mold contains the wear element and channels the casting metal into that element and forms its external metal mass into an appropriately shaped arm, shell or other structural shape.

As shown in phantom in FIG. 1, such a mold 36 contacts the ceramic wear body to form a series of recesses, both within and outside of the ceramic wear body, which are to be occupied by the metal. This external mold or shell 36 may be formed by three-dimensional powder printing at the same time as the basic ceramic wear surface element is formed, by printing further patterns built-up of powdered ceramic-forming material outside and beyond the wear surface block as the computer controlled nozzle scans the powder bed. This forms an outer mold part as described in applicant's aforesaid co-pending patent application, and this outer part serves the function of a conventional investment casting mold, for those metal portions of the prosthesis which are to be cast against the ceramic wear surface. The outer mold is broken away after the prosthesis is cast, leaving only the inner wear surface portion incorporated in a metal casting. Alternatively, the outer mold may be formed separately and attached to a previously-formed and fired ceramic wear body, since, in general the outer mold need not be as fully fired as the portion which is incorporated as a wear surface. In each of FIGS. 2A, 2B, and 3 such an outer mold 36 is indicated in phantom showing its position for defining the metal portions. Runners or sprue holes 38 are positioned to achieve proper filling of irregular shapes. It will therefore be understood that the mold 36 may exist integrally with the surface wear element 3 during an early fabrication stage either initially as the ceramic/mold elements are printed, or after a separate initial firing in which the wear surface element is fired to a ceramic-forming temperature. Once casting is complete, the outer mold is then removed from the ceramic wear and cast metal portions during a finishing and clean-up operation.

It will be further understood that the invention is broadly applicable to articulation components of arbitrary design for implantation. Thus, rather than the conventional ball and socket joint described above, the fabrication of a cast metal skeleton or frame interfitted with ceramic wear element allows the use of shapes which, although long known in the area of industrial machinery to confer significant mechanical advantages, such as torque transfer or load bearing, have previously been difficult to implement as an implantable prosthetic with suitable strength or other physical properties because of the limitations imposed by physical characteristics of biocompatible materials and fabrication processes. It also allows use of known prosthetic designs which previously could not readily be implemented in metal/ceramic materials, or unitary metal/ceramic constructions.

Figure 4:
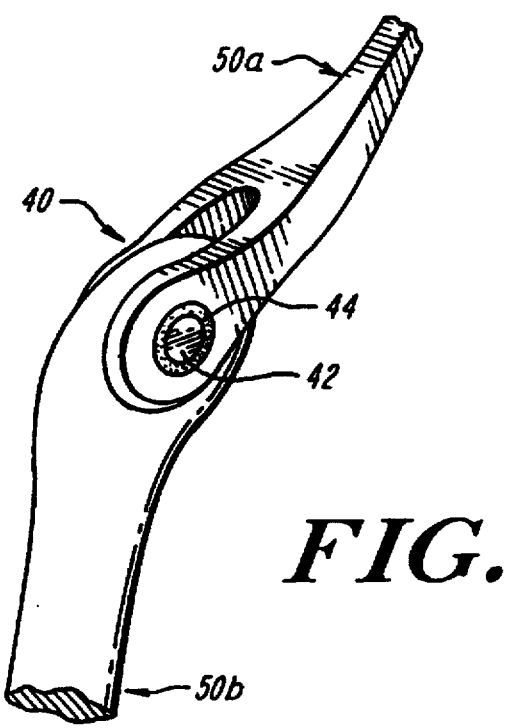
FIG. 4 illustrates another articulated prosthesis component.

For example, as shown in FIG. 4, one such articulation component is a trunion articulation 40, wherein a cylindrical peg or shaft 42 rotates in a journal 44. These bearing elements may each readily be formed with thick, hard and smooth ceramic surface portions or their bearing faces, and metallic endo- or exo-skeletons incorporated in load-bearing shafts 50a, 50b, as indicated in the FIGURE to achieve an implantable prosthesis of high strength with excellent wear properties and toughness.

Figure 5A:
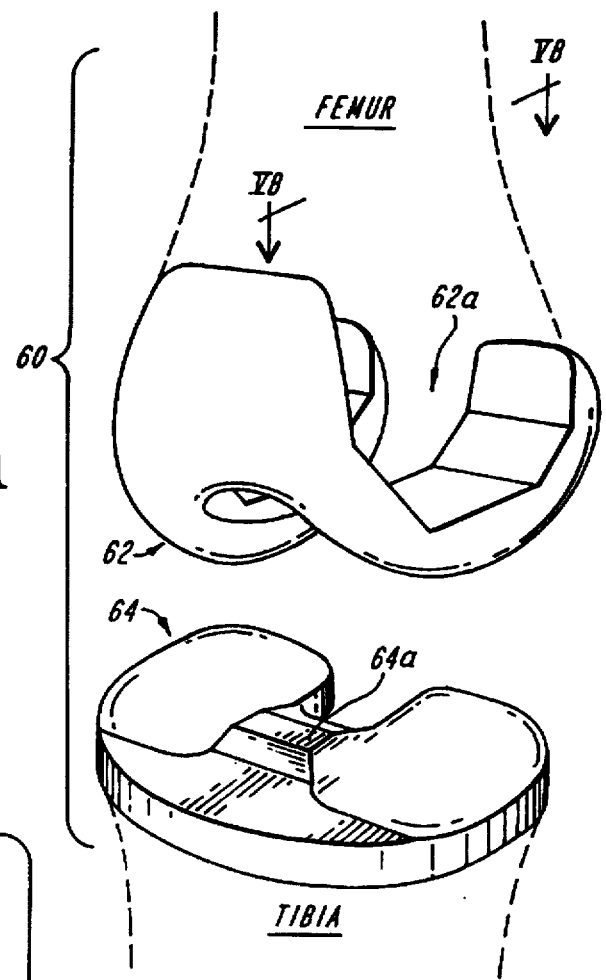
FIGS. 5A and 5B illustrate another prosthesis.
Figure 5B:
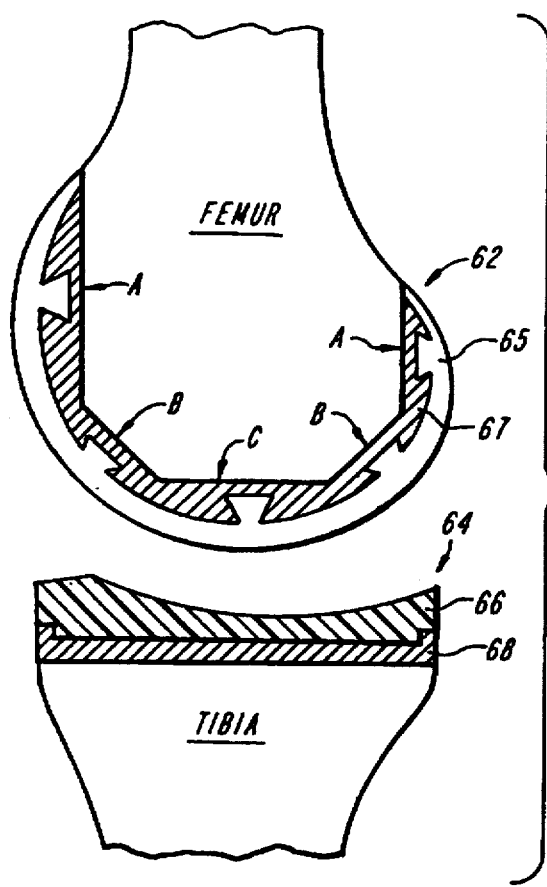

In addition to hinged or trunion-type constructions, the present invention advantageously achieves long-wearing and dependable articulations in which rolling, sliding, or some combination of rolling and sliding are effected at the interface of mating joint pieces. FIGS. 5A and 5B show a perspective view and a front to back vertical section, respectively, through a knee prosthesis 60 having such articulation.

As shown, the prosthesis comprises an upper part 62 attached to the femur which rests on a lower part 64 attached to the tibia. The femoral articulation element 62 is a ceramic wear-surface component with a generally saddle-shaped appearance, and with a central slot 62a that in use serves as an alignment aid, while the tibial component 64 is a mating table with a corresponding central protrusion 64a aligned with the slot. Sectional view, FIG. 5B, shows more detailed structural aspects of these elements.

The ceramic upper component 64 includes a ceramic shell 65 which constitutes the load-bearing wear surface and is dovetailed or otherwise interfitted to (e.g. by mushroomshaped protrusions) and integral with a metal exoskeleton or backing plate 67. Backing plate 67 has undercut openings or depressions that rigidly interconnect along a generally radial direction with the ceramic shell. Furthermore, the skeletal plate 67 has a regular geometric interior shape, which allows the end of the femur to be readily sawn, shaved or otherwise cut to fit precisely into and attach to the plate 67. The illustrated recess in the plate 67 includes a cylindrical bore section "A", a regularly beveled edge "B" and a flat bottom "C", allowing the bone end to be readily tailored to fit the recess. Section "A" might also be a generally flat rectangular section rather than a cylindrical one. What is important is that the metal plate 67 provides a strong and tough skeleton to secure the wear surface at the bone end.

On the tibial side, the articulation component includes a metal platform 68, having a wear surface insert 66 on which the upper component 62 rests. Here, the insert is preferably a thick polyethylene pad, which serves to moderate any sharp impacts so that the ceramic top articulation does not crack or shatter in use. Post-operatively, the installed prosthetic relies on normal connective tissue structures to secure the tibial and femoral components together, and the joint performs a rolling, or rolling/sliding motion with a slight natural degree of torsional looseness about the alignment slot 62a.

The invention being thus disclosed, variations and modifications will occur to those skilled in the art, and such variations are intended to be within the scope of the invention as set forth in the claims appended hereto.

What is claimed is:

1. An implantable bone prosthesis comprising a support body formed from a ceramic material, the support body having a load-bearing wear surface for bearing a load on the prosthesis, and a structural body, wherein the support body and the structural body are interdigitated with respect to each other and wherein at least 50% of the surface area of the load-bearing wear surface is a continuous and uninterrupted ceramic surface.

2. An implantable bone prosthesis according to claim 1, wherein the structural material forms a branching skeleton of structural material.

3. An implantable bone prosthesis according to claim 1, wherein the structural body is tougher than the ceramic load-bearing wear surface.

4. An implantable bone prosthesis according to claim 1, wherein the ceramic load-bearing wear surface is substantially harder than the structural body.

5. An implantable bone prosthesis according to claim 1, wherein the wear surface has at least one property selected from the group consisting of: small grain size, high hardness, long wear properties, and corrosion resistance; while the structural body has at least one property selected from the group consisting of: high stiffness, high tensile strength, durability and toughness.

6. An implantable bone prosthesis forming at least a component of a replacement joint of enhanced strength and wear properties, comprising a multi-apertured body formed of ceramic material and including continuous surface area constituting a hard external wear surface consisting of said ceramic material, and a support body which is flowed into and hardened in place within apertures of the ceramic body to provide structural supporting members for said ceramic body, said supporting members extending and contacting the ceramic body along a direction which allows movement when said support body shrinks such that the members harden to support said ceramic body and provide strength thereto without introducing destructive stress, wherein said support body includes a shell extending over a broad continuous area as a supporting sheet next to said wear surface.

7. An implantable bone prosthesis comprising a wear body consisting of ceramic material and including a first, continuous, non-apertured ceramic surface, and a second surface opposite the first surface, the second surface defining apertures in the wear body; and a support body extending into the apertures of the second surface of the wear body.

8. An implantable bone prosthesis according to claim 7, wherein said support body includes a branching structure extending within said body.

9. An implantable bone prosthesis according to claim 7, wherein the non-apertured ceramic surface is a rounded load-bearing surface of an articulation.

10. An implantable bone prosthesis according to claim 7, wherein the non-apertured ceramic surface is a spherical bearing surface.

11. An implantable bone prosthesis according to claim 7, wherein the non-apertured ceramic surface is a cylindrical bearing surface.

12. An implantable bone prosthesis according to claim 7, wherein the non-apertured ceramic surface is a rolling wear surface.

13. An implantable bone prosthesis according to claim 7, wherein the non-apertured ceramic surface is one of a rolling wear surface, a sliding wear surface, a pivoting wear surface, and a rolling/sliding wear surface.

* * * * *